US006933321B2

(12) United States Patent
Labrie et al.

(10) Patent No.: US 6,933,321 B2
(45) Date of Patent: Aug. 23, 2005

(54) ANTIANDROGENIC BIPHENYLS

(75) Inventors: Fernand Labrie, Sainte-Foy (CA); Shankar Mohan Singh, Sainte-Foy (CA); Van Luu-The, Sainte-Foy (CA)

(73) Assignee: Endorecherche, Inc. (CA)

( * ) Notice: Subject to any disclaimer, the term of this patent is extended or adjusted under 35 U.S.C. 154(b) by 0 days.

(21) Appl. No.: 10/369,267

(22) Filed: Feb. 14, 2003

(65) Prior Publication Data

US 2004/0006134 A1 Jan. 8, 2004

Related U.S. Application Data

(60) Provisional application No. 60/357,785, filed on Feb. 15, 2002.

(51) Int. Cl.$^7$ ............................................. A61K 31/277

(52) U.S. Cl. ......................... 514/646; 514/716; 514/721

(58) Field of Search .................. 514/646, 716, 514/721; 558/388, 408, 410; 568/642

(56) References Cited

U.S. PATENT DOCUMENTS

| | | | | |
|---|---|---|---|---|
| 3,281,280 A | * | 10/1966 | Schaefer | 429/347 |
| 3,742,951 A | | 7/1973 | Zaffaroni | 128/268 |
| 3,797,494 A | | 3/1974 | Zaffaroni | 128/268 |
| 4,285,829 A | * | 8/1981 | Eidenschink et al. | 252/299.63 |
| 4,568,343 A | | 2/1986 | Leeper et al. | 604/896 |
| 5,064,654 A | | 11/1991 | Berner et al. | 424/448 |
| 5,071,644 A | | 12/1991 | Viegas et al. | 514/772.7 |
| 5,071,657 A | | 12/1991 | Oloff et al. | 424/486 |
| 5,518,654 A | * | 5/1996 | Coates | 252/299.66 |
| 5,559,277 A | * | 9/1996 | Beller et al. | 585/469 |
| 6,060,503 A | | 5/2000 | Labrie et al. | 514/428 |

FOREIGN PATENT DOCUMENTS

| | | |
|---|---|---|
| DE | 32 47 215 A | 6/1984 |
| DE | 196 07 135 C | 4/1997 |
| EP | 0 279 982 | 8/1988 |
| EP | 0 757 982 A | 2/1997 |
| JP | 05-273771 | * 10/1993 |
| WO | WO 94 05153 A | 3/1994 |
| WO | WO 94 25431 A | 10/1994 |
| WO | WO-99/55668 | * 11/1999 |
| WO | WO 01 70678 A | 9/2001 |

OTHER PUBLICATIONS

Database CA 'Online! Chemical Abstracts Service, Columbus, Ohio, US; Toyama, Takeshi et al: "Biaryl compounds and diaryl ethers as uricosuric agents" retrieved from STN, Database accession No. 132:73651, XP002237333, see compound RN= 42289–54–3, abstract & JP 2000 001431 A (Kotobuki Seiyaku Co., Ltd., Japan) Jan. 7, 2000.

Database CA 'Online! Chemical Abstracts Service, Columbus, Ohio, US; Parkinson, Andrew et al: "Induction of rat liver microsomal cytochrome P–450 isozymes and epoxide hydrolase by a series of 4'–substituted–2,3,4,5–tetrachloro-biphenyls" retrieved from STN, Database accession No. 110:149290, XP002237334, See compound RN=88966–74–9 abstract & Toxicology (1988), 53(2–3), 289–300.

American Chemical Society Division of Medicinal Chemistry, Abstracts, 222$^{nd}$ ACS National Meeting, Chicago, IL, Aug. 26–30, 2001, No. 201. "Synthesis and SAR of 5–aryl Oxindoles and 5–aryl Indolines as Novel Non–Steroidal PR Antagonists", John W. Ullrich, et al.

American Chemical Society Division of Medicinal Chemistry, Abstracts, 222$^{nd}$ ACS National Meeting, Chicago, IL, Aug. 26–30, 2001, No. 204. "Structure Activity Relationship of Triaryl and Biaryl Carboxy Acid and Acylsulfonamide Analogs on the Human EP$_3$ Prostano Receptor", Michel Gallant, et al.

Online!, J. Biol. Chem. vol. 277, Issue 32, 28909–28915, Aug. 9, 2002, Evidence That the Human Gene for Prostate Short–chain Dehydrogenase/Reductase (PSDRI) Encodes a Novel Retinal Reductase (RAIRI), Natalia Y. Kedishvili, et al.

Bioorganic & Medicinal Chemistry Letters II (2001), pp. 1709–1712 "Biphenyls as Surrogates of the Steroidal Backbone. Part 1: Synthesis and Estrogen Receptor Affinity of an Original Series of Polysubstituted Biphenyls", Dominique Lesuisse, et al.

Bioorganic & Medicinal Chemistry Letters II (2001), pp. 1713–1716 "Biphenyls as Surrogates of the Steroidal Backbone. Part 2: Discovery of a Novel Family of Non–steroidal 5–α–Reductase Inhibitors", Dominique Lesuisse, et al.

(Continued)

*Primary Examiner*—Fiona T. Powers
(74) *Attorney, Agent, or Firm*—Ostrolenk, Faber, Gerb & Soffen, LLP

(57) ABSTRACT

Biphenyl derivatives are disclosed for use in the treatment of androgen-dependent diseases, such as prostate cancer, benign prostatic hyperplasia, precocious puberty, polycystic ovarian syndrome, acne, hirsutism, seborrhea, androgenic alopecia and premature male baldness. For example, some preferred compounds having the structure:

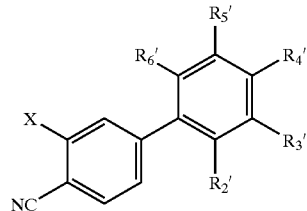

are formulated together with pharmaceutically acceptable diluent or carrier for topical use in the treatment of acne, hirsutism, seborrhea or androgenic alopecia, or for systemic use in the treatment of androgen-dependent prostate cancer.

40 Claims, No Drawings

OTHER PUBLICATIONS

Online—Cancer Research 61, pp. 1611–1618, Feb. 15, 2001, American Association for Cancer Research, Molecular Biology and Genetics "Prostrate Short–Chain Dehydrogenase Reductase 1 (PSDR1): A New Member of the Short–Chain Steroid Dehydrogenase/Reductase Family Highly Expressed in Normal and Neoplastic Prostate Epithelium", Biaoyang Lin, et al.

J. Med. Chem. 2000, 43, pp. 4354–4358, "Biarylpropysulfonamides as Novel, Potent Potentiators of 2–Amino–3–(5–methyl–3–hydroxyisoxazol–4–yl)– propanoic Acid (AMPA) Receptors", Paul L. Ornstein, et al.

"Apparent Positive Cooperative Effects in Cyclic AMP and Corticosterone Production by Isolated by Adrenal Cells in Response to ACTH Analogues", (1974) Endocrinology vol. 94, No. 5, pp. 1427–1437, D. Robard, (Reproduction Research Branch, National Institute of Child Health and Human Development, National Institutes of Health, Bethesda, Maryland 20014).

Bioorganic & Medicinal Chemistry 8 (2000) pp. 1087–1109, "Biaryl Diacid Inhibitors of Human s–$PLA_2$ with Anti–Inflammatory Activity", Dane M. Springer, et al.

Medline, "Development of methods for the quantitative in vitro analysis of androgen–dependent and autonomous Shionogi carcinoma 115 cells", E.R. Stanley, et al., Abstract.

Bioorganic & Medicinal Chemistry 8 (2000), pp. 1245–1252, Novel Imidazolyl and Triazolyl Substituted Biphenyl Compounds: Synthesis and Evaluation as Nonsteroidal Inhibitors of Human 17α–Hydroxylase–C17, 20–Lyase (P450 17), Yan Zhuang, et al.

* cited by examiner

ANTIANDROGENIC BIPHENYLS

This application claims priority of U.S. provisional application No. 60/357,785, filed Feb. 15, 2002.

BACKGROUND OF THE INVENTION

This invention relates to novel inhibitors of sex steroid activity such as antiandrogenic compounds having effective antagonistic activity while substantially lacking agonistic effects. More particularly, the invention relates to certain biphenyl derivatives and their metabolites which block androgen action by acting, among other mechanisms, through the androgen receptors but not activating such receptors. These compounds are useful in the treatment of (or reduction of risk of acquiring) androgen-exacerbated disease, discussed herein.

BRIEF DESCRIPTION OF THE PRIOR ART

During the treatment of certain androgen-dependent diseases, it is important to greatly reduce or, if possible, to eliminate androgen-induced effects. For this purpose, it is desirable to both block access to the androgen receptors with "antiandrogens", thus preventing androgens from binding and activating those receptors, and also to reduce the concentration of androgens available to activate the receptors. It is possible that, even in the absence of androgens, unoccupied androgen receptors may be biologically active. Hence, antiandrogens which bind and block the receptors may produce better therapeutic results than therapy which only inhibits androgen production.

Antiandrogens may have a significant therapeutic effect in slowing or stopping the progress of androgen-dependent diseases, e.g. diseases whose onset or progress is aided by androgen receptor or androgen receptor modulator activation.

It is desired that an antiandrogen used in therapy to reduce androgen receptor activation have both good affinity for the androgen receptor and a substantial lack of inherent androgenic activity. The former refers to the ability of an antiandrogen to bind to the androgen receptor, and thus to block access to the receptor by androgens. The latter refers to the effect the antiandrogen has on the receptor once it binds thereto. Some antiandrogens may possess inherent androgenic activity ("agonistic activity") which undesirably activates the very androgen receptors whose activation they are intended to prevent. In other words, an antiandrogen with intrinsic androgenic activity may successfully bind to androgen receptors, desirably blocking access to those receptors by natural androgens, yet may undesirably itself activate the receptor.

Known non-steroidal antiandrogens such as flutamide, casodex and anandron lack undesirable androgenic activity, but may not have receptor affinity as good as steroidal antiandrogens (i.e. androgen derivatives having a steroidal nucleus that is modified to provide antiandrogenic activity). Steroidal antiandrogens, however, are believed more likely to possess undesirable agonistic characteristics. Steroidal antiandrogens are also expensive to synthesize.

Thus there is a need in the Art for inexpensive non-steroidal antiandrogens having good affinity to androgen receptor and substantially lacking undesirable agonistic characteristics.

For the treatment of androgen-dependent skin diseases, most of known antiandrogens such as flutamide have unwanted systemic activity when applied on the skin and cannot generally be used. For androgen-dependent skin-related diseases such as acne, hirsutism, seborrhea, androgenic alopecia, premature male baldness, it is believed that antiandrogens must not penetrate in the body in significant amounts and have antiandrogenic effect in other tissues than on the area of the skin where they are applied.

Thus, there is also a need in the Art for nonsteroidal antiandrogens having good affinity for androgen receptor and substantially lacking undesirable agonistic and systemic activity.

SUMMARY OF THE INVENTION

It is an object of the present invention to provide biphenyl antiandrogens, having good affinity for the androgen receptor, while substantially lacking androgenic activity. These antiandrogens may be useful in the treatment of androgen-dependent diseases as described in more detail infra.

In one aspect, the invention provides an antiandrogenic compound of the molecular formula:

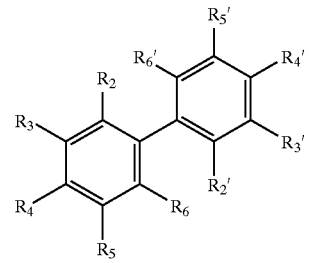

I

Wherein $R_2$, $R_3$, $R_5$ and $R_6$ are independently selected from the group consisting of hydrogen, fluoride, chloride, bromide, iodide, cyanide, $C_1$–$C_3$ alkyl, $C_1$–$C_3$ fluoroalkyl, nitro, carboxamide,

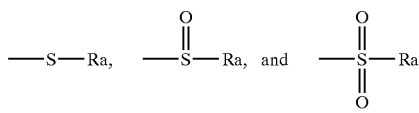

(Ra being $C_1$–$C_3$ alkyl);
Wherein $R_4$ and $R_4'$ are independently selected from the group consisting of hydrogen, fluoride, chloride, bromide, iodide, cyanide,

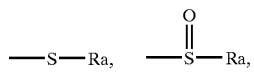

and

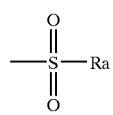

(Ra being $C_1$–$C_3$ alkyl); —ORb, —PO(ORb)$_2$, —C≡C—Rb, (Rb being $C_1$–$C_6$ alkyl), $C_2$–$C_3$ trifluorohydroxyalkyl, trifluoromethyl, nitro, amine, acetylamine, sulphamine, and ureide;
Wherein at least one of $R_4$ and $R_4'$ is not hydrogen;
Wherein $R_2'$ and $R_6'$ are independently selected from the group consisting of hydrogen, fluoride, chloride, bromide, iodide, cyanide, trifluoromethyl, nitro, carboxamide,

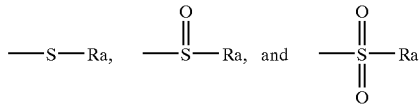

(Ra being $C_1$–$C_3$ alkyl);
Wherein $R_3'$ and $R_5'$ are independently selected from the group consisting of hydrogen, fluoride, chloride, bromide, iodide, cyanide, $C_2$–$C_3$ trifluorohydroxyalkyl, $C_1$–$C_3$ alkyl, $C_1$–$C_3$ fluoroalkyl, nitro, and carboxamide.

In another aspect, the invention provides topical or systemic pharmaceutical compositions containing the antiandrogens of the invention together with pharmaceutically acceptable diluents or carriers.

In another aspect, the novel antiandrogens, or pharmaceutical compositions containing them, are used in the treatment or prevention of androgen-dependent skin related diseases such as acne, hirsutism, seborrhea, androgenic alopecia, premature male baldness and the like.

In another aspect, they are used in the treatment or prevention of androgen-sensitive systemic diseases such as prostate cancer or benign prostatic hyperplasia, precocious puberty, polycystic ovarian syndrome.

It is another object to provide treatment and prevention regimens for androgen sensitive diseases which regimens include use of androgen receptor antagonists disclosed herein, as part of a combination therapy which further utilizes other active compounds such as 5alpha-reductase inhibitor, 17beta-hydroxysteroid dehydrogenase type 5 inhibitors and PSDR-1 inhibitors.

In one embodiment of the invention provides a pharmaceutical composition comprising a pharmaceutically acceptable diluent or carrier and a therapeutically effective amount of at least one antiandrogenic compound of the molecular formula:

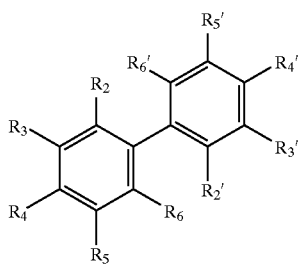

I

Wherein $R_2$, $R_3$, $R_5$ and $R_6$ are independently selected from the group consisting of hydrogen, fluoride, chloride, bromide, iodide, cyanide, $C_1$–$C_3$ alkyl, $C_1$–$C_3$ fluoroalkyl, nitro, carboxamide,

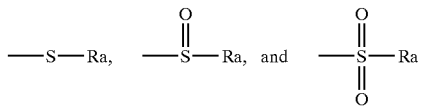

(Ra being $C_1$–$C_3$ alkyl);
Wherein $R_4$ and $R_4'$ are independently selected from the group consisting of hydrogen, fluoride, chloride, bromide, iodide, cyanide,

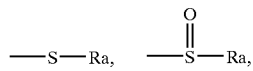

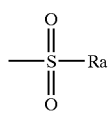

(Ra being $C_1$–$C_3$ alkyl), —ORb, —PO(ORb)$_2$, —C≡C—Rb, (Rb being $C_1$–$C_6$ alkyl), $C_2$–$C_3$ trifluorohydroxyalkyl, trifluoromethyl, nitro, amine, acetylamine, sulphamine, and ureide;

Wherein at least one of $R_4$ and $R_4'$ is not hydrogen;
Wherein $R_2'$ and $R_6'$ are independently selected from the group consisting of hydrogen, fluoride, chloride, bromide, iodide, cyanide, trifluoromethyl, nitro, carboxamide,

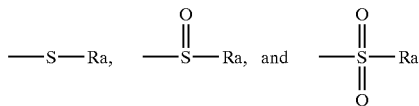

(Ra being $C_1$–$C_3$ alkyl);
Wherein $R_3'$ and $R_5'$ are independently selected from the group consisting of hydrogen, fluoride, chloride, bromide, iodide, cyanide, $C_2$–$C_3$ trifluorohydroxyalkyl, $C_1$–$C_3$ alkyl, $C_1$–$C_3$ fluoroalkyl, nitro, and carboxamide;

DETAILED DESCRIPTION OF THE PREFERRED EMBODIMENTS

The antiandrogens and pharmaceutical compositions containing them, may be utilized in accordance with the invention in the treatment of androgen-sensitive diseases whose progress or onset is aided by activation of androgen receptors or androgen receptor modulators.

These include but are not limited to prostate cancer, benign prostatic hyperplasia, acne, seborrhea, hirsutism, androgenic alopecia, premature male baldness, precocious puberty, polycystic ovarian syndrome and the like.

It is preferred that the $R_4$ or $R_4'$ substituent of the biphenyl antiandrogen be a cyanide group. In some embodiments, the antiandrogenic compound has the following molecular formula:

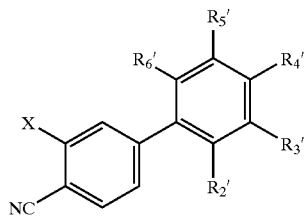

Wherein X is selected from the group consisting of fluoride, chloride, bromide, iodide, and trifluoromethyl,

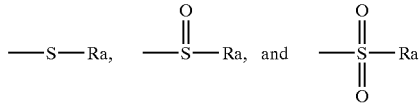

(Ra being $C_1$–$C_3$ alkyl);
Wherein $R_2'$ and $R_6'$ are independently selected from the group consisting of hydrogen, fluoride, chloride, bromide, iodide, cyanide, trifluoromethyl, nitro, carboxamide,

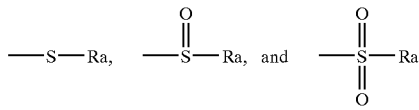

(Ra being $C_1$–$C_3$ alkyl);
Wherein $R_3'$ and $R_5'$ are independently selected from the group consisting of hydrogen, fluoride, chloride, bromide, iodide, cyanide, $C_2$–$C_3$ trifluorohydroxyalkyl, $C_1$–$C_3$ alkyl, $C_1$–$C_3$ fluoroalkyl, nitro, and carboxamide;

Wherein $R_4'$ is selected from the group consisting of hydrogen, fluoride, chloride, bromide, iodide, cyanide, $C_2$–$C_3$ trifluorohydroxyalkyl, trifluoromethyl, amide, sulfamine,

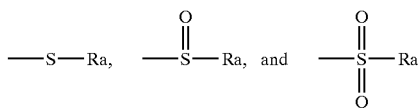

(Ra being $C_1$–$C_3$ alkyl) and nitro.

The following compound, EM-4283 (3-chloro-2',4'-difluoro-biphenyl-4-carbonitrile), is especially preferred for systemic used:

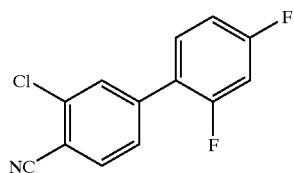

The following compound, EM-4977 (3-chloro-2',6'-difluoro-biphenyl-4-carbonitrile), is especially preferred for topical application:

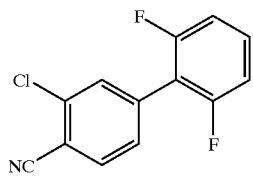

The antiandrogens of the invention are preferably formulated together with pharmaceutically acceptable diluent, excipient or carrier (including capsules) into pharmaceutical compositions at conventional antiandrogen concentrations for antiandrogens used in the prior art. The attending clinician may elect to modify the concentration and/or dosage in order to adjust the dose to the particular response of each patient. Preferably, the attending clinician will, especially at the beginning of treatment, monitor an individual patient's overall response and serum levels of antiandrogen (in comparison to the preferred serum concentrations discussed below), and monitor the patient's overall response to treatment, adjusting dosages as necessary where a given patients' metabolism or reaction to treatment is atypical. As discussed in more detail below, carriers, excipients or diluents include solids and liquids. When a composition is prepared other than for immediate use, an art-recognized preservative is typically included (e.g. benzyl alcohol). The novel pharmaceutical compositions of the invention may be used in the treatment of androgen-related diseases, or to reduce the likelihood of acquiring such diseases. When administered systemically (e.g., for treatment of prostate cancer, benign prostatic hyperplasia, precocious puberty, polycystic ovarian syndrome and other diseases not primarily affecting the skin) conventional diluents or carriers which are known in the art to be pharmaceutically acceptable for systemic use are used, e.g., saline, water, aqueous ethanol, oil, etc. The carrier is often a mixture of ingredients.

When formulated for systemic use, the antiandrogens may be prepared for administration in conventional ways such as orally or by injection. The antiandrogen can be administered, for example, by the oral route. The compounds of the present invention may be formulated with conventional pharmaceutical excipients, (e.g. spray dried lactose and magnesium stearate) into tablets or capsules for oral administration. Of course, taste-improving substances can be added in the case of oral administration forms. When capsules for oral ingestion are desired, any pharmaceutical capsules known in the art may be filled with the active ingredients of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g. of hard gelatin, as well as closed soft-gelatin capsules comprising a softener or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

A dry delivery system, as described in U.S. Pat. Nos. 3,742,951, 3,797,494 or 4,568,343 may be used.

Alternatively, the active ingredient may be placed into a transdermal patch having structures known in the art, for example, structures such as those set forth in E.P. Patent No. 0279982.

Solvents or devices as described in U.S. Pat. Nos. 5,064,654, 5,071,644 or 5,071,657 can also be used to facilitate transdermal penetration when systemic effects are desired. When used to treat systemic diseases, the site of application on the skin should be changed in order to avoid excess local concentration of biphenyls.

In some embodiments, the antiandrogens of the invention are utilized for the treatment of androgen related diseases of the skin such as acne, seborrhea, hirsutism, androgenic alopecia and premature male baldness. When used for any of these purposes, the antiandrogens are preferably administered topically together with a conventional topical carrier or diluent. When used topically, it is preferred that the diluent or carrier does not promote transdermal penetration of the active ingredients into the blood stream or other tissues where they might cause unwanted systemic effects.

When the compound is administered in a cutaneous or topical carrier or diluent, the carrier or diluent may be chosen from any known in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin, lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols.

Usually, the topical carrier includes both water and alcohol in order to maximize the hydrophylic and lipophylic solubility, e.g. a mixture of ethanol or isopropanol with water.

A topical carrier may also include various other ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The concentration of active ingredient in the ointment, cream, gel or lotion is typically from about 0.1 to 20 percent preferably between 1 and 10 percent and most preferably 5 percent (by weight relative to the total weight of the lotion, cream, gel or ointment). Within the preferred ranges, higher concentrations allow a suitable dosage to be achieved while applying the lotion, ointment, gel or cream in a lesser amount or with less frequency.

Several non-limiting examples describe the preparation of a typical lotion and gel, respectively. In addition to these infra vehicles, one skilled in the art may choose other vehicles in order to adapt to specific dermatologic needs.

When antiandrogens are administered systemically, they are preferably administered orally or parenterally. Naturally, topical administration is preferred when the desired site of action is the skin.

Concentration of the active antiandrogen varies in a known manner depending upon the method of administering the pharmaceutical composition. A composition suitable for oral administration may preferably include at least one antiandrogen wherein the total concentration of all such antiandrogens in said pharmaceutical composition is from about 1% to 95% of the composition (by weight), and preferably from about 5% to about 20%. Where a combination of antiandrogens is used, the total dosage of the sum of all antiandrogens should be equal to the dosage range recited above. Blood level of the antiandrogen is a preferred criteria of adequate dosage which takes into account individual variation in absorption and metabolism.

When prepared for parental injection, the antiandrogen is preferably added at a concentration between about 0.1 mg/ml and about 100 mg/ml (preferably about 2.0 mg/ml to about 10 mg/ml).

When systemic activity is desired, it is necessary only that the antiandrogen be administered in a manner and at a dosage sufficient to allow blood serum concentration to obtain desired levels. Serum antiandrogen concentration should typically be maintained between 10 and 2000 micrograms per liter, preferably between 100 and 1000 micrograms per liter and most preferably between 200 and 500 micrograms per liter. Adequate serum levels may also be assessed by a patient's response to therapy.

For typical patients, the appropriate dosage of the antiandrogen to achieve desired serum concentration is between 10 and 2000 milligrams of active ingredient per day per 50 kg of body weight when administered orally. When administered by injection, about 1 to 2000 mg per day per 50 kg of body weight is recommended, preferably from 10 to 100.

For topical use lotion, ointment, gel or cream should be thoroughly rubbed into the skin so that no excess is plainly visible, and the skin is preferably not washed in that region for at least 30 minutes. The amount applied should provide at least 0.02 milligrams of antiandrogen per square centimeter (preferably from 0.1 to 1 mg/cm$^2$) per application. It is desirable to apply the topical composition to the effected region from 1 to 6 times daily, e.g. 3 times daily at approximately regular intervals.

The protein Prostate Short-Chain Dehydrogenase Reductase 1 (PSDR1) was first identified as a Short-Chain Steroid Dehydrogenase/Reductase that is highly expressed in Normal and Neoplastic Prostatic Epithelium (Lin B, Cancer Research 61:1611–8, 2001) without enzymatic activity characterization. Recently, using the protein overexpressed in SF9 insect cells, the enzyme has been found to have retinal reductase activities catalyzing the transformation of retinal into retinol (Kedishvili-N Y et al., JBC 277, 28909–15, 2002). The authors concluded that the enzyme is selective for retinoids and does not possess any significant oxidative or reductive activity toward the functional hydroxyl or ketone groups in positions 3, 17, or 20 of steroids.

In contrast, using human embryonic kidney cells stably transfected with human PSDR1 cDNA in culture, we have found that the enzyme possesses a predominant 17β-hydroxysteroid dehydrogenase activity, selective for 5α-reduced steroids, catalyzing the transformation of 5α-androstane-3,17-dione (5α-dione) into 5α-androstane-17-ol-3-one (dihydrotestosterone, DHT) and of 5α-androstane-3α-ol-17-one (ADT) into 5α-androstane-3α, 17β-diol (3α-diol).

Using RealTime PCR to quantify the MRNA expression levels of the enzyme in various human and mouse tissues, we have found that this enzyme is expressed in a wide range of tissues. It is strongly expressed in the human prostate, and at a lower level in the human liver, adrenal and placenta. In the mouse, it is highly expressed in the testis and in the preputial and clitoridal glands. It is also expressed in mouse seminal vesicles, epididymis, hypophysis, adrenals, liver, kidney, thymus, adipose tissue, skin, lung, esophagus, colon, mammary gland, uterus, vagina, and ovary.

These results strongly suggest that this enzyme plays an important role in the formation of the most potent natural androgen DHT.

In some embodiments of the invention, the antiandrogen of the invention is used in combination with another active ingredient as part of a combination therapy. For example, the novel antiandrogen may be utilized together with a separate 5α-reductase inhibitor, a type 5 17β-hydroxysteroid dehydrogenase inhibitor, or a Prostate Short-Chain Dehydrogenase Reductase 1 inhibitor which may be incorporated into the same pharmaceutical composition as is the antiandrogen, or which may be separately administered. Combination therapy could thus include treatment with one or more compounds which inhibit the production of dihydrotestosterone or its precursors. In some preferred embodiments of the invention, the topical pharmaceutical composition further includes an inhibitor of steroid 5α-reductase activity. One such inhibitor ("Propecia or Proscar") is commercially available form Merck Sharp and Dohme. Inhibitors of type 5 17β-hydroxysteroid dehydrogenase (more particularly compound EM-1404) are disclosed in the international publication WO 97/11162. EM-1791, one of inhibitors of Prostate Short-Chain Dehydrogenase Reductase 1 (PSDR1) is easily synthesized from benzopyran compounds disclosed in the U.S. Pat. No. 6,060,503 as described in the following scheme;

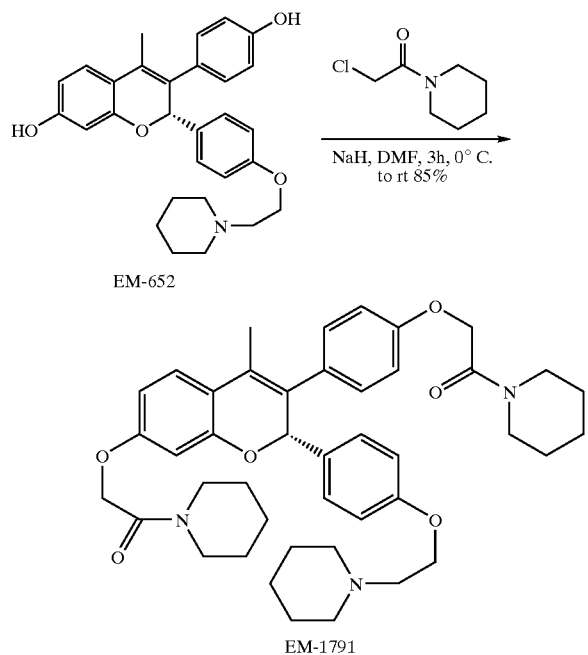

Preferred Antiandrogens

When 5alpha-reductase inhibitors are used in combination therapies, in accordance with the invention described herein, oral dosage is preferably between 0.1 mg and 100 mg per day per 50 kg body weight, more preferably between 0.5 mg/day and 10 mg/day, for example 1 mg per day of finasteride.

When type 5 17beta-hydroxysteroid dehydrogenase inhibitors are used in combination therapies, in accordance with the invention described herein, oral dosage is preferably between 5 mg and 500 mg per day per 50 kg body weight, more preferably between 10 mg/day and 400 mg/day, for example 300 mg per day of EM-1404.

When PSDR-1 inhibitors are used in combination therapies, in accordance with the invention described herein, oral dosage is preferably between 10 mg and 2000 mg per day per 50 kg body weight, more preferably between 100/day and 1000 mg/day, for example 500 mg per day of EM-1791.

A patient in need of treatment or reducing the risk of onset of a given disease is one who has either been diagnosed with such disease or one who is susceptible to acquiring such disease. The invention is especially useful for individuals who, due to heredity, environmental factors or other recognized risk factor, are at higher risk than the general population of acquiring the conditions to which the present invention relates.

Except where otherwise stated, the preferred dosage of the active compounds of the invention is identical for both therapeutic and prophylactic purposes. The dosage for each active component discussed herein is the same regardless of the disease being treated (or prevented).

Where two are more different active agents are discussed as part of a combination therapy herein (e.g. an enzyme inhibitor and an antiandrogen), a plurality of different compounds are administered rather than a single compound having multiple activities.

Except where otherwise indicated, the term "compound" and any associated molecular structure may include any possible stereoisomers thereof, in the form of a racemic mixture or in optically active form.

Except where otherwise noted or where apparent from context, dosages herein refer to weight of active compounds unaffected by pharmaceutical excipients, diluents, carries or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent" or "carrier" include such non-active ingredients as are typically included, together with active ingredients in such dosage forms in the industry.

All of the active ingredients used in any of the combination therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one other container with respect to active ingredients contained therein. Two or more different containers are used in the combination therapies of the invention. Combination therapies discussed herein also include use of one active ingredient of the combination in the manufacture of a medicament for the treatment (or prevention) of the disease in question where the treatment or prevention further includes another active ingredient or strategy of the combination.

Set forth in the table below is a list of compounds which we have found to be useful as antiandrogens. The table also includes in vitro determination of androgenic/antiandrogenic activity on mouse mammary carcinoma Shionogi cells and in vivo determination of systemic antiandrogenic activity of immature male rats. It is believed that the rat assays are better for predicting systemic efficacy, while the Shionogi assay is better for predicting efficacy against skin diseases.

TABLE 1

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-3234 | O$_2$N–C$_6$H$_4$–C$_6$H$_4$–OMe | <0.2 | >500 | ND | ND |
| EM-3393 | F$_3$C, O$_2$N substituted biphenyl-OMe | 0.4 | 129 | 0 | 0 |
| EM-3394 | F$_3$C, NC substituted biphenyl-OMe | 1.1 | 49.5 | 0 | 0 |
| EM-3703 | F$_3$C, NC substituted biphenyl-Cl | 0.3 | 97 | 15 | 18 |
| EM-3704 | NC–C$_6$H$_4$–C$_6$H$_4$–OMe | <0.2 | >500 | 0 | 13 |
| EM-3705 | F$_3$C, NC substituted biphenyl-F | 0.7 | 129 | 71 / 84 | 101 / 99 |
| EM-3729 | F$_3$C, NC substituted biphenyl-CN | <0.2 | >500 | 4 | 0 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-3730 | [structure: 3'-CF3, 4'-CN biphenyl with 4-CN] | 0.2<br>0.6 | 190<br>152 | 154<br>113 | 99<br>102 |
| EM-3732 | [structure: 3'-CF3, 4'-CN biphenyl with 4-SCH3] | <0.2 | >500 | 54 | 55 |
| EM-3747 | [structure: 3'-CF3, 4'-CN biphenyl with 5-Cl, 2-OMe] | <0.2 | >500 | 13 | 0 |
| EM-3812 | [structure: 3'-CF3, 4'-CN biphenyl with 4-S(O)CH3] | <0.2 | >500 | 50 | 54 |
| EM-3814 | [structure: 3'-CF3, 4'-CN biphenyl with 4-N(CH3)2] | 0.9 | 150 | 41 | 0 |
| EM-3971 | [structure: 3'-CF3, 4'-CN biphenyl with 4-CONH2] | <0.2 | >500 | 11 | 0 |
| EM-3974 | [structure: 3'-CF3, 4'-CN biphenyl with 3,5-diF] | <0.2 | >500 | 13 | 0 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-3975 | | 0.77 | 131 | 102 | 98 |
| EM-3976 | | <0.2 | >500 | 30 | 35 |
| EM-3977 | | <0.2 | >500 | 27 | 0 |
| EM-3978 | | <0.2 | >500 | 41 | 24 |
| EM-3979 | | <0.2 | >500 | 52 | 40 |
| EM-3986 | | <0.2 | >500 | 29 | 9 |
| EM-3987 | | <0.2 | >500 | 0 | 0 |

TABLE 1-continued
| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity $IC_{50}$ (nM) 4 | Prostate % efficacy versus flu per os DHT 5 | SV % efficacy versus flu per os DHT 6 |
| EM-3993 | 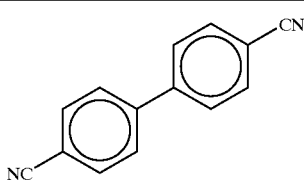 | <0.2 | >500 | 57 | 61 |
| EM-3998 | 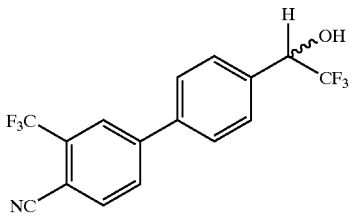 | <0.2 | >500 | 47 | 71 |
| EM-4004 | 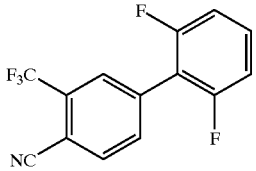 | <0.2 | >500 | 14 | 32 |
| EM-4012 | 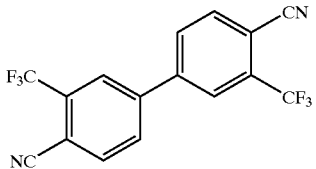 | <0.2 | >500 | 28 | 58 |
| EM-4026 | 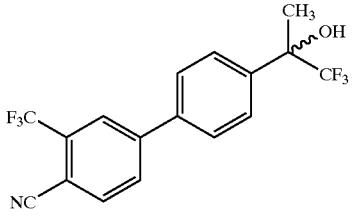 | <0.2 | >500 | 37 | 52 |
| EM-4034 | 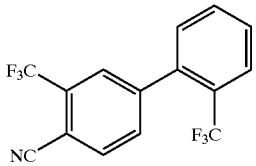 | <0.2 | >500 | 0 | 0 |
| EM-4036 | 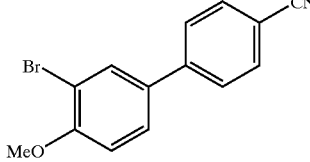 | <0.2 | >500 | 0 | 0 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity $IC_{50}$ (nM) 4 | Prostate % efficacy versus flu per os DHT 5 | SV % efficacy versus flu per os DHT 6 |
| EM-4046 | | <0.2 | >500 | 0 | 13 |
| EM-4047 | | <1 | >100 | 68 | 59 |
| EM-4049 | | <0.2 | >500 | 0 | 21 |
| EM-4051 | | <0.2 | >500 | 19 | 59 |
| EM-4056 | | <0.2 | >500 | 21 | 18 |
| EM-4057 | | 1.2 | 84 | 0 | 15 |
| EM-4065 | | <0.2 | >500 | 60 | 85 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4068 | | 0.9 | 96 | 0 | 0 |
| EM-4069 | | 0.7 | 110 | 0 | 0 |
| EM-4071 | | 2.5 | 33 | 24 | 41 |
| EM-4079 | | 0.8 | 78 | 43 | 25 |
| EM-4080 | | 0.6 | 102 | 4 | 0 |
| EM-4093 | | <0.2 | >500 | 18 | 45 |
| EM-4096 | | <0.2 | >500 | 33 | 0 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4108 | | 0.6 | 112 | 73 | 95 |
| EM-4116 | | <0.2 | >500 | 38 | 49 |
| EM-4118 | | <0.2 | >500 | 0 | 10 |
| EM-4149 | | <0.2 | >500 | 65 | 104 |
| EM-4154 | | 0.7 | 145 | 60 | 86 |
| EM-4171 | | 0.2 | 943 | 188 | 112 |
| EM-4174 | | 2.1 | 77 | 38 | 53 |

TABLE 1-continued
|  |  | IN VITRO Shionogi | | IN VIVO Rats | |
| --- | --- | --- | --- | --- | --- |
| NAME 1 | STRUCTURE 2 | A = Ki OH-Flu/ Ki compound 3 | Antiandrogenic activity $IC_{50}$ (nM) 4 | Prostate % efficacy versus flu per os DHT 5 | SV % efficacy versus flu per os DHT 6 |
| EM-4177 | 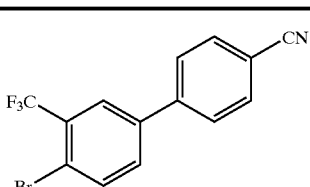 | <0.2 | >500 | 10 | 34 |
| EM-4180 | 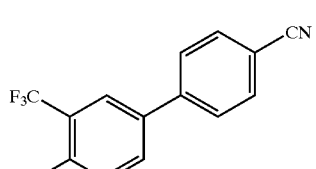 | <0.2 | >500 | 10 | 27 |
| EM-4185 | 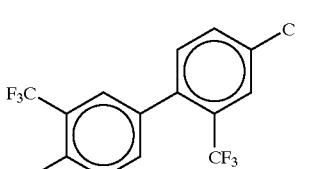 | 0.7 | 193 | 127 | 102 |
| EM-4186 | 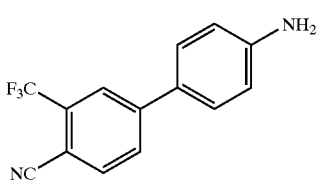 | 1.2 | 118 | 13 | 19 |
| EM-4189 | 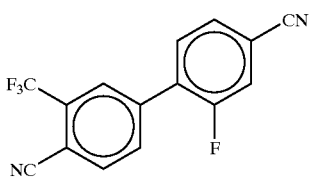 | 1.1 | 132 | 154 | 106 |
| EM-4190 | 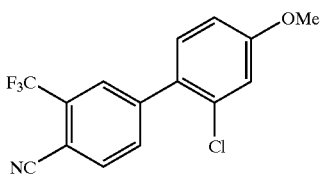 | 0.9 | 162 | 35 | 27 |
| EM-4203 | 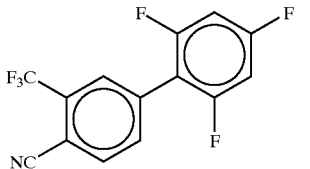 | 0.6 | 280 | 102 | 91 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4205 | [structure] | 3.0 | 52 | 152 | 106 |
| EM-4206 | [structure] | <0.2 | >500 | 48 | 29 |
| EM-4216 | [structure] | <0.2 | >500 | 0 | 68 |
| EM-4227 | [structure] | 1.2 | 121 | 56 | 91 |
| EM-4230 | [structure] | <0.2 | >500 | 26 | 49 |
| EM-4234 | [structure] | 3.2 | 43.2 | 122 | 101 |
| EM-4243 | [structure] | <0.2 | >500 | 51 | 42 |

TABLE 1-continued

| | | IN VITRO Shionogi | | IN VIVO Rats | |
|---|---|---|---|---|---|
| NAME 1 | STRUCTURE 2 | A = Ki OH-Flu/ Ki compound 3 | Antiandrogenic activity $IC_{50}$ (nM) 4 | Prostate % efficacy versus flu per os DHT 5 | SV % efficacy versus flu per os DHT 6 |
| EM-4244 | | <0.2 | >500 | 53 | 19 |
| EM-4246 | | <0.2 | >500 | 42 | 0 |
| EM-4248 | | <0.2 | >500 | 31 | 23 |
| EM-4249 | | <0.2 | >500 | 18 | 28 |
| EM-4253 | | <0.2 | >500 | 53 | 62 |
| EM-4255 | | <0.2 | >500 | 76 | 77 |
| EM-4263 | | <0.2 | >500 | 20 | 6 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4264 | | 1.6 | 54 | 98 | 90 |
| EM-4265 | | 0.7 | 116 | 0 | 24 |
| EM-4280 | | <0.2 | >500 | 76 | 81 |
| EM-4281 | | 0.6 | 145 | 137 | 100 |
| EM-4282 | | <0.2 | >500 | 89 | 87 |
| EM-4283 | | 2.3 | 37 | 120 | 99 |
| EM-4285 | | <0.2 | >500 | 7 | 0 |
| EM-4288 | | 4.4 | 28 | 73 | 64 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4292 | | <0.2 | >500 | 56 | 60 |
| EM-4296 | | <0.2 | >500 | 60 | 87 |
| EM-4320 | | <0.2 | >500 | 87 | 101 |
| EM-4338 | | <0.2 | >500 | 28 | 43 |
| EM-4344 | | <0.2 | >500 | 2 | 19 |
| EM-4633 | | 0.8 | 96 | 0 | 16 |
| EM-4792 | | <0.2 | >500 | 49 | 76 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4833 | | <0.2 | >500 | 4 | 20 |
| EM-4841 | | <0.2 | >500 | 140 | 99 |
| EM-4844 | | <0.2 | >500 | 111 | 96 |
| EM-4845 | | <0.2 | >500 | 163 | 110 |
| EM-4849 | | <0.2 | >500 | 121 | 102 |
| EM-4851 | | <0.2 | >500 | 75 | 86 |
| EM-4855 | | <0.2 | >500 | 194 | 103 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4856 | F$_3$C—[ring]—CN, [ring]—F, CONH-Bu | <0.2 | >500 | 123 | 96 |
| EM-4863 | F$_3$C—[ring]—CN, [ring]—F, CONH—[ring]—Cl | 0.3 | 161 | 0 | 19 |
| EM-4864 | F$_3$C—[ring]—CN, [ring]—F, CONH—[ring] | <0.2 | >500 | ND | ND |
| EM-4865 | F$_3$C—[ring]—CN, [ring]—F, CONMe$_2$ | <0.2 | >500 | 189 | 100 |
| EM-4866 | F$_3$C—[ring]—CN, [ring]—F, CONHEt | <0.2 | >500 | 191 | 106 |
| EM-4867 | F$_3$C—[ring]—CN, [ring]—NO$_2$, F, F | <0.2 | >500 | 0 | 0 |
| EM-4871 | MeO—[ring]—Br, [ring]—F, F | <0.2 | >500 | 29 | 29 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4905 | [structure] | <0.2 | >500 | ND | ND |
| EM-4925 | [structure] | <0.2 | >500 | 0 | 0 |
| EM-4947 | [structure] | <0.2 | >500 | 0 | 3 |
| EM-4948 | [structure] | <0.2 | >500 | 76 | 71 |
| EM-4961 | [structure] | <0.2 | >500 | 151 | 114 |
| EM-4977 | [structure] | 12 | 12.8 | 0 | 11 |
| EM-4979 | [structure] | <0.2 | >500 | 151 | 104 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-4980 | | <0.2 | >500 | 60 | 55 |
| EM-5002 | | <0.2 | >500 | 0 | 0 |
| EM-5003 | | <0.2 | >500 | 16 | 0 |
| EM-5004 | | <0.2 | >500 | 62 | 0 |
| EM-5014 | | <0.2 | >500 | ND | ND |
| EM-5018 | | <0.2 | >500 | ND | ND |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity IC$_{50}$ (nM) 4 | Prostate % efficacy versus flu per os DHT 5 | SV % efficacy versus flu per os DHT 6 |
| EM-5019 | | <0.2 | >500 | ND | ND |
| EM-5020 | | <0.2 | >500 | ND | ND |
| EM-5021 | | <0.2 | >500 | 31 | 76 |
| EM-5038 | | <0.2 | >500 | 33 | 22 |
| EM-5082 | | <0.2 | >500 | 0 | 12 |
| EM-5083 | | <0.2 | >500 | 0 | 27 |

TABLE 1-continued

| NAME 1 | STRUCTURE 2 | IN VITRO Shionogi | | IN VIVO Rats | |
|---|---|---|---|---|---|
| | | A = Ki OH-Flu/ Ki compound 3 | Antiandrogenic activity $IC_{50}$ (nM) 4 | Prostate % efficacy versus flu per os DHT 5 | SV % efficacy versus flu per os DHT 6 |
| EM-5085 | 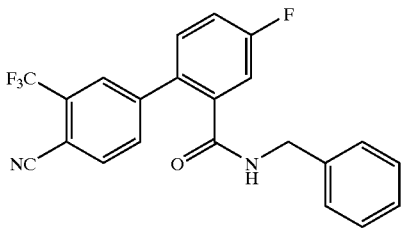 | <0.2 | >500 | 138 | 107 |
| EM-5086 | 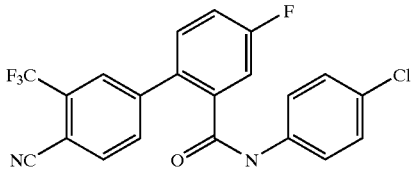 | <0.2 | >500 | 44 | 44 |
| EM-5093 | 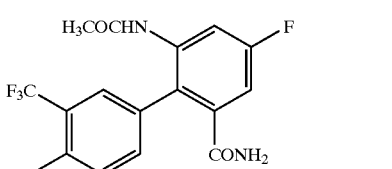 | <0.2 | >500 | 0 | 15 |
| EM-5094 | 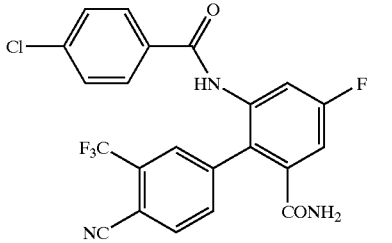 | <0.2 | >500 | 23 | 34 |
| EM-5111 | 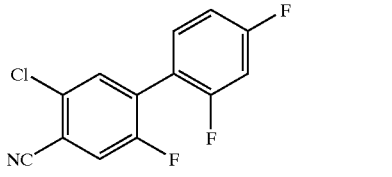 | <0.2 | >500 | 60 | 36 |
| EM-5112 | 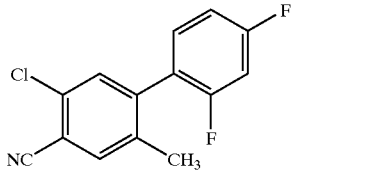 | 1.1 | 97 | 92 | 72 |

Legend:

Column 3 represents the ratio of Inhibition Constant (Ki value) of the inhibition of DHT-stimulated Shionogi mouse mammary carcinoma cell number for hydroxy-flutamide versus the tested compound. Higher values are preferable.

Column 4 represents the dose (expressed in nM) that inhibits of 50% ($IC_{50}$) the DHT-stimulated Shionogi mouse mammary carcinoma cell number. Lower values are preferable.

Column 5 represents the % of antiandrogenic efficacy in rat prostate, relatively to the percentage of inhibition of flutamide calculated by the formula:

% efficacy versus Flu=100×% inhib (compound)/% inhib (Flu).

Where the percentage of inhibition (% inhib) is calculated by the following formula:

% Inhib=100−[W (compound)−W (control)/W (DHT)−W (control)]×100.

W is the weight of the prostate.
Higher values are preferable.
Column 6 represents the % of antiandrogenic efficacy in rat seminal vesicle, relatively to the percentage of inhibition of flutamide calculated by the formula:

% efficacy versus Flu=100×% inhib (compound)/% inhib (Flu).

Where the percentage of inhibition (% inhib) is calculated by the following formula:

% Inhib=100−[W (compound)−W (control)/W (DHT)−W (control)]×100.

W is the weight of the seminal vesicle.
Higher values are preferable.
ND: not determined

TABLE 2

| NAME | Dose ($\mu$g) | Antiandrogenic activity in Hamster Ear Area Inhibition. Vs Control (%) |
|---|---|---|
| 1 | 3 | 4 |
| EM-4004 | 10 | 60 |
| EM-4046 | 30 | 5 |
| EM-4057 | 10 | 64 |
| EM-4068 | 30 | 15 |
| EM-4080 | 30 | 5 |
| EM-4174 | 10 | 86 |
| EM-4186 | 30 | 0 |
| EM-4265 | 30 | 0 |
| EM-4863 | 30 | 21 |
| EM-4977 | 10 | 73 |
|  | 1 | 25.9 |
|  | 3 | 48.0 |
|  | 10 | 62.9 |

Column 2 represent the daily dose for 14 days of tested compound dissolved in ten $\mu$l solution of acetone:ethanol:propylene Glycol (1:1:2; v:v:v) applied onto a region between the two cartilage ridges of the ventral surface of left pinna.

Column 3 represents the percentage of inhibition of the area of the sebaceous glands of the left ear of the treated animals versus the area of the sebaceous glands of the left ear of the control animals.

Efficacy of the Preferred Inhibitors

A In vitro Assays of Androgenic/Antiandrogenic Activity of Biphenyls

Androgenic/antiandrogenic activity of preferred compounds has been measured using the Shionogi mouse mammary carcinoma cells.

1. Materials

Minimal essential culture medium (MEM), non-essential amino acids, and fetal calf serum were purchased from Flow Laboratories. In order to remove endogenous steroids, serum was incubated overnight at 4° C. with 1% activated charcoal (Norit A, Fisher) and 0.1% Dextran T-70 (Pharmacia). A 2-h supplementary adsorption was performed at 25° C. in order to further remove protein-bound steroids. Serum was also inactivated by a 20-min incubation at 56° C.

5α-dihydrotestosterone (DHT) was obtained from Steraloids. The antiandrogen hydroxyflutamide (OH-FLU) was kindly supplied by Drs. T. L. Nagabuschan and R. Neri (Schering Corporation, Kenilworth, U.S.A.).

2. Cell Dispersion, Culture and Cloning

Shionogi male mice bearing androgen-sensitive mammary tumors were obtained from Drs. Keishi Matsumoto, Osaka, Japan, and Yvonne Lefebvre, Ottawa, Canada. For primary culture, tumors were excised and washed in ice-cold sterile 25 mM Hepes buffer (137 mM NaCl; 5 mM KCl; 0.7 mM $Na_2HPO_4$; 10 mM glucose, pH 7.2). After mincing with scissors, the tumor minces were digested for 2 h at 37° C. in Hepes buffer containing 3.8 mg/ml collagenase (Clostridium, Boehringer), 1.5 mg/ml hyaluronidase II (Sigma), and 3% bovine serum albumin fraction V (Schwartz-Mann). Dispersed cells were collected by centrifugation (500×g for 10 min), washed twice by suspension in minimal essential medium (MEM) containing 5% dextran-coated charcoal-treated fetal calf serum (DCC-FCS), 1% non-essential amino acids, 10 IU/ml penicillin, 50 $\mu$g/ml streptomycin, and 100 nM dihydrotestosterone (DHT) (Steraloids).

Cells were plated in the same medium at a density of 75 000 cells/ml in 75 $cm^2$ flasks under an atmosphere of 5% carbon dioxide in air at 37° C. The medium was changed weekly. Biphenyls were dissolved in ethanol and kept in stock solutions chosen to yield final ethanol concentrations less than 0.01% in the culture medium. Such a concentration of ethanol does not affect cell growth.

Cells were subcultured at near-confidence by gentle digestion in a solution of 0.1% pancreatin (Flow Laboratories) in Hepes buffer containing 3 mM ethylenediaminetetraacetic acid (EDTA) (pH 7.2). Cells were pelleted by centrifugation, resuspended in culture medium, counted in a Coulter counter, and replated as described above. Soft agar cloning was performed as described (Stanley et al., Cell 10: 35–44, 1977) in the presence of 100 nM DHT.

3. Measurement of Cell Growth

Cells were plated in 24-well plates at a density of 20 000 cells/well. The indicated increasing concentrations of agents were added to triplicate dishes, and cells were grown for 10–12 days with changes of medium every 3–4 days. Cell number was measured by direct counting in a Coulter counter.

4. Calculations and Statistical Analysis $IC_{50}$ values of biphenyls were calculated according to a least-square regression as described by Rodbard, Endocrinology. Statistical significance was calculated according to Kramer multiple-range test.

B Systemic Antiandrogenic Activity (Immature Male Rats)

1. Animals

Immature male rats (Crl:CD(SD)Br) 22 to 24-day old were obtained from Charles-River, Inc. (St-Constant, Quebec, Canada) and housed up to 5 per cage in plastic bins in a temperature (23±1° C.)- and light (12 h light/day, lights on at 7h15)-controlled environment. The rats were fed rodent chow and tap water ad libitum. The day following their arrival, the animals were orchidectomized (CX) under Isoflurane anesthesia via scrotal route and randomly assigned to groups of 5 animals. One silastic implant of dihydrotestosterone (DHT; length of implant 1 cm) was inserted subcutaneously in the dorsal area of animals at the time of orchidectomy. One group of 5 animals was CX only as control (no DHT implant inserted).

2. Treatments

To evaluate the antiandrogenic activity, tested compounds were administered orally by gavage once daily at a dose of 0.5 mg/animal for 7 days (SD 1 to 7). Compounds were solubilized (when possible) in dimethylsulfoxide (DMSO, 10% final concentration) and administered as suspension in 0.4% methylcellulose. Rats in CX control and CX+DHT control groups received the vehicle alone during the 7-day period. One group of animals received the antiandrogen Flutamide as reference. The animals were killed by cervical dislocation under isoflurane anesthesia on the 8th morning following castration. The ventral prostate and seminal vesicles were rapidly dissected and weighed.

3. Calculations and Statistical Analysis

The percentage of inhibition (% inhib) is calculated by the following formula:

% Inhib=100−[W (compound)−W (control)/W (DHT)−W (control)]×100.

This percentage is reported as % of efficacy, relatively to the percentage of inhibition of flutamide calculated by the formula:

% efficacy versus Flu=100×% inhib (compound)/% inhib (Flu).

W is the weight of the prostate or the seminal vesicle.

Some non-limiting examples of preferred active compounds are discussed below together with preferred synthesis techniques.

C—In vivo Assessment of Topical Antiandrogenic Activity

The antiandrogenic activity of compounds for topical use was determined using the ear sebaceous glands model in the male hamster.

1. Animals

Male Golden Syrian Hamsters (SYR) of 110–120 g were obtained from Harlan Sprague-Dawley (Madison, USA) and housed up to 2 per plastic cage in a temperature (22±3° C.) and light (12 h light/day, lights on at 7h15)-controlled environment. The hamsters were fed with Certified Rodent Diet 5002 (pellet) and had access to tap water ad libitum. The animals were acclimatized for at least five days prior to beginning the study. Animals were randomly assigned to groups of eight hamsters. One group of hamsters were castrated under isoflurane-induced anesthesia on the day of dosing initiation (SD 1) and used as control group.

2. Treatments

To evaluate the antiandrogenic activity, the tested compounds were applied topically on the inner part of the left ear, once daily, for 14 days. A ten-$\mu$L solution of acetone:ethanol:propylene Glycol (1:1:2; v:v:v) containing 0.1, 0.3 or 1.0 mg/mL of the tested compound was carefully applied onto a region between the two cartilage ridges of the ventral surface of the left pinna. For animals of the castrated and intact control groups, one ten-$\mu$L vehicle was applied onto the left ear. No solution was applied on the right ear.

3. Post-Mortem Observations and Measurements

On Study Day 15, the hamsters were euthanized by cervical dislocation under isoflurane anesthesia. The left and right ears were collected attached together by the head skin, flat fixed on a paper and then immersed in 10% neutral buffered formalin. Punctures making a circular hole of 6 mm were made on the flat fixed ear in the region where the solution has been applied. These punch-made specimens were collected from each ear. Using a scalpel blade, the collected 6 mm round ear specimens were cut in the middle between the two cartilage ridges. The two equal parts of the ear round specimens were embedded in paraffin. After processing the tissue, the two parts were vertically embedded parallel to each other in such a way that the flat 6 mm area was facing out. From each paraffin block, one section (5 $\mu$m thick) was cut and collected on a glass slide. Thus, each slide contained two elongated sections of 6 mm length. Slides were stained with hematoxylin and eosin.

4. Analysis of Sebaceous Gland Area

Using the video camera and the lens number X5 of the light microscope, the resulting field appearing on the screen has a length of 0.953 mm. When the first 6 mm long section was examined from the left to the right, the first and second fields were ignored and the third and fourth fields were captured for analysis by the image analyzer. Each field has the length of 0.953 mm. With the help of the screen mouse, the sebaceous glands within the whole field length (0.953 mm) were marked. Also, an area having the length of the whole field and the height between stratum granulosum and the upper edge of the cartilage was drawn.

The total area of the sebaceous glands ($\mu m^2$) in each examined field was calculated by the Image Analyser. We also measured the total area, which has the length of 0.953 mm and the height between stratum granulosum and the cartilage. In addition, the percentage of the area occupied by the glands was obtained. Thus, for each ear, two sections were cut and two fields from each section were analyzed. The total of the four readings was averaged and the mean standard error of the mean was calculated by the image analyzer. The results were expressed in $\mu m^2$ as the total surface of glands per field and also as percentage of the area occupied by the glands in the tissue.

EXAMPLES OF SYNTHESIS OF PREFERRED INHIBITORS

Proton NMR spectra were recorded on a Brucker AC-F 300 instrument or a Brucker Avance 400 MHz. The following abbreviations have been used: s, singlet; d, doublet; dd, doublet of doublet; t, triplet; q, quadruplet; and m, multiplet. The chemical shifts ($\delta$) were referenced to chloroform (7.26 ppm for $^1$H and 77.00 ppm for $^{13}$C) and were expressed in ppm. Thin-layer chromatography (TLC) was performed on 0.25 mm Kieselgel 60F254 plates (E. Merck, Darmstadt, FRG). For flash chromatography, Merck-Kieselgel 60 (230–400 mesh A.S.T.M.) was used. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Starting materials and reagents were available from Aldrich Chemical Company, Inc. (Milwaukee, Wis.).

List of Abbreviations

DMAP 4-dimethylaminopyridine
DMF dimethyformamide
THF Tetrahydrofuran
Tf$_2$O Triflic anhydride Example 1

Example 1 is a general scheme of some preferred biphenyls of the invention using as key step a Suzuki coupling.

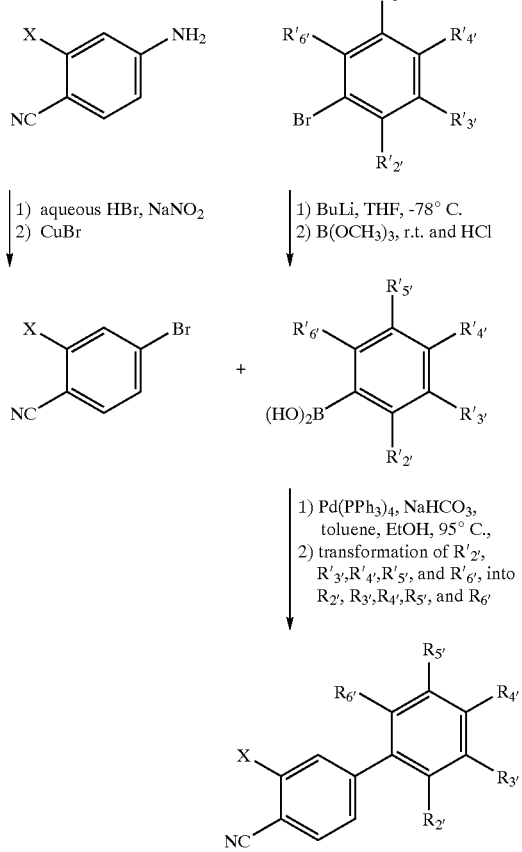

Example 2

Synthesis of 4'-Cyano-4-fluoro-3'-trifluoromethyl-biphenyl-2-carboxylic acid amide (EM-4171)

4-Bromo-2-trifluoromethylbenzonitrile:

In a round bottom flask, 4-cyano-3-trifluoromethylaniline (20 g, 107.5 mmol) was solubilized in 300 mL of 47% aq HBr. This solution was cooled to 0° C. in an ice bath and NaNO$_2$ (22.2 g, 322 mmol) was added slowly. Then CuBr (46.3 g, 322.5 mmol) was added slowly. After the addition, the ice bath was removed and the mixture was stirred at 20° C. for 3 hr. The mixture was cooled to 0° C. in an ice bath and 500 mL of water were added to get a yellow precipitate. Solid was filtered and washed successively with 10% aq. HCl (50 mL) and water (100 mL), and dried to give the product (23.5 g, 87%), $^1$H NMR (300 MHz, Acetone-d$_6$)δ: 8.19 (s, 1H, C$_3$—H), 8.16 (d, 1H, J=8 Hz, C$_6$—H), 8.05 (d, 1H, J=8 Hz, C$_5$—H).

4-Fluoro-2-methoxyphenylboronic acid:

In a round bottom flask dried under argon, were added 2-bromo-5-fluoroanisole (5.9 g, 29 mmol) and dry THF (50 mL). The solution was cooled to −78° C. and BuLi (17.4 mL, 43.5 mmol) was added slowly. After 30 min at −78° C., trimethyl borate (4.9 mL, 43.5 mmol) was added and then the mixture was allowed to warm to room temperature (1.3 hr). After then the solution was cooled to 0° C. and 20 mL of 10% aq.HCl was added. THF was removed and brine (50 ml) was added. The mixture was extracted twice with ether. The organic layer was washed first with 10% aq. hydrochloric acid and then brine. The ether layer was dried (MgSO$_4$) and evaporated to give a yellow solid (4 g, 82%), $^1$H NMR (400 MHz, acetone-d$_6$)δ: 7.84 (t, 1H, J=8 Hz, C$_6$—H), 6.85 (dd, J=12, 2 Hz, C$_3$—H), 6.76 (td, J=8, 2 Hz C$_5$—H).

A General Method for Suzuki Couplings:

4'-Fluoro-2'-methoxy-3-trifluoromethyl-biphenyl-4-carbonitrile:

In a round bottom flask under argon, 4-bromo-2-trifluoromethylbenzonitrile (1 g, 4 mmol) was solubilized in a mixture of toluene (55 mL) and EtOH (20 mL). Aq. NaHCO$_3$ (20 ml, 5 eq., 0.8 M solution) and 4-fluoro-2-methoxyphenylboronic acid (816 mg, 4.8 mmol) were added. The mixture was degassed under the stream of argon for 10 min. Then Pd(PPh$_3$)$_4$ (462 mg, 0.4 mmol) was added and the mixture was heated at 95° C. for 2 hr. After it was cooled, the mixture was poured in brine and extracted with CH$_2$Cl$_2$. This organic layer was dried (MgSO$_4$), filtered and evaporated. Chromatography on a silica gel (250 ml, EtOAc:hexanes, 1:9), gave a white solid (951 mg, 81%), $^1$H NM (300 MHz, acetone-d$_6$)δ: 8.02–8.14 (m, 3H, C$_{2,5,6}$—H), 7.53 (dd, 1H, J=8, 7 Hz, C$_6$'—H), 7.03 (dd, 1H, J=11, 2 Hz, C$_3$'—H), 6.89 (td, 1H, J=8, 2Hz, C$_5$'—H).

4'-Fluoro-2'-hydroxy-3-trifluoromethyl-biphenyl-4-carbonitrile:

To solution of biphenyl (1.06 g, 3.58 mmol) in CH$_2$Cl$_2$ (3 mL) was added BBr$_3$ (7.5 ml, 7.5 mmol, 1M in CH$_2$Cl$_2$). The solvent was removed slowly to dryness by heating at 60° C. for 1 hr. The mixture was then heated at 60° C. for an additional 30 min. After cooling, the mixture in CH$_2$Cl$_2$ was washed with water and brine. Drying (MgSO$_4$), filtration and evaporation gave a white solid (1 g, 99%), $^1$H NMR (300 MHz, acetone-d$_6$)δ: 9.50 (bs, 1H, OH), 8.08–8.20 (m, 3H, C$_{2,5,6}$—H), 7.53 (t, 1H, J=7 Hz, C$_6$'—H), 6.78–6.86 9 (m, 2H, C$_{3',5}$—H).

Trifluoromethanesulfonic acid-4'-cyano-4-fluoro-3'-trifluoromethyl-biphenyl-2-yl ester:

To a solution of 2-hydroxybiphenyl (1 g, 3.56 mmol) in dry CH$_2$Cl$_2$ (100 mL) were added dry NEt$_3$ (992 μL, 7.12 mmol) and DMAP (44 mg, 0.356 mmol) at room temperature. At 0° C., Tf$_2$O (900 μL, 5.3 mmol) was added slowly and the reaction was stirred for 45 min at 1° C. The mixture was quenched with 50 mL of saturated aq. NH$_4$Cl and extracted with CH$_2$Cl$_2$. The organic layer was dried (MgSO$_4$). After filtration and evaporation of the solvent the, residue was chromatographed on a silica gel (EtOAc:hexanes, 1:2.3) to give an oil (1.46 g, 99%), $^1$H NMR (400 MHz, acetone-d$_6$) δ: 7.98 (d, 1H, J=8 Hz, C$_5$'—H), 7.90 (s, 1H, C$_{2'}$—H)), 7.79 (d, 1H, J=8 Hz, C$_6$'—H)), 7.52 (dd, 1H, J=6, 8 Hz, C$_6$—H)), 7.22–7.34 (m, 2H, C$_{3',5}$'—H).

4'-Cyano-4-fluoro-3-trifluoromethyl-biphenyl-2-carboxylic acid methyl ester:

In an argon dried round bottom flask, the ester was dissolved in dry DMF (80 mL). Then dry MeOH (25 mL) dry Et$_3$N (1.5 ml. 3 eq.) and dppp (87 mg, 0.212 mmol, 0.06 eq.) were added. After then Pd(OAC)$_2$ (55 mg, 0.247 mmol) was added and the mixture was heated for 1 hr at 95° C. with a stream of carbon monooxide and then mixture was heated in a carbon monooxide atmosphere for an additional 30 min. After cooling, the contents were quenched with 100 mL of ice and a stream of argon was passed through for 15 min to remove the carbon monooxide. The mixture was then extracted twice with CH$_2$Cl$_2$ and dried (MgSO$_4$). After filtration and evaporation, the crude product was chromatographed on 100 mL of a silica gel (EtOAc:hexanes, 1:4) to give of a crystalline product (999 mg, 88%), $^1$H NMR (300 MHz, acetone-d$_6$) δ: 8.14 (d, 1H, J=8 Hz, C$_5$'—H)), 7.93 (s, 1H, C$_2$'—H)), 7.85 (d, 1H, J=8 Hz, C$_6$'—H)), 7.71–7.75 (dd, 1H, J=2.6, 8 Hz, C$_3$—H)), 7.50–7.53 (m, 2H, C$_{5,6}$—H)), 3.70 (s, 3H, COOCH$_3$)).

4'-Cyano-4-fluoro-3'-trifluoromethyl-biphenyl-2-carboxylic acid amide (EM-4171):

In a Schlenk tube equipped with a magnetic stirrer, ammonia (60 mL) was condensed at −78° C. Then NaCN (8.6 g, 176 mmol) was added followed by biphenyl-2-carboxy ester (1.5 g, 4.64 mmol) in 80 mL of dry MeOH. The Schlenk tube was heated at 70° C. for 16 hr. After cooling, the tube was opened carefully in a dry ice/$CH_3CN$ bath (−45° C.) and the ammonia was evaporated slowly with stirring. The mixture was poured in brine and extracted with $CH_2Cl_2$ and dried ($MgSO_4$). After filtration and evaporation, the residue was chromatographed on 200 ml of a silica gel (EtOAc:hexanes 1:1.5) to give a white crystalline solid (999 mg, 76%), IR (KBr, $cm^{-1}$) 3431.3 3299.7 3181.6 2237.0 1668.9 1326.7 1179.7 1130.6 823.0, $^1H$ NMR (400 MHz, acetone-$d_6$) δ 8.14 (d, 1H, J=8 Hz, $C_5'$—H), 8.00 (s, 1H, $C_2'$—H), 7.93 (d, 1H, J=8 Hz, $C_6'$—H), 7.62 (d, 1H, J=8 Hz, $C_6$—H), 7.44 (t, 1H, J=8 Hz, $C_5$—H), 7.39 (d, 1H, J=8 Hz, $C_3$—H). $^{13}C$.NMR (acetone-$d_6$) δ: 108.93, 115.75, 116.06, 116.17 (CN), 117.51, 117.79, 121.86, 125.47, 127.97, 128.03, 129.09, 131.64, 132.07, 132.49, 132.91, 133.35, 133.47, 133.94, 134.18, 135.86, 139.997, 146.35, 161.65, 164.95, 169.57 (CO).

Example 3

Synthesis of 3-chloro-2',4'-difluoro-biphenyl-4-carbonitrile (EM-4283)

3-Chloro-2',4'-difluorobiphenyl-4-carbonitrile (EM-4283):

In a round bottom flask, 4-bromo-2-chlorobenzonitrile (3 g, 13.85 mmol), 2,4-difluorophenylboronic acid (2.63 g, 16.63 mmol) and $K_3PO_4$ (8.83 g, 41.56 mmol) were added in dry DMF (50 mL). The mixture was purged under argon for 30 min and $Pd(PPh_3)_4$ (1.6 g, 1.38 mmol) was added. The mixture was heated for 48 hr at 80 C. Water (100 mL) was added and the aq layer was extracted with $CH_2Cl_2$ (3×50 mL). The organic layer was washed with brine (3×50 mL), dried, evaporated and purified on silica gel (EtOAc/hexanes:1/19) to give the product (1 g, 29%), $^1H$.NMR (acetone-$d_6$) δ: 7.2–7.28 (m, 2H), 7.72–7.79 (m, 2H), 7.91 (t, 1H, J=1.4 Hz), 8.02 (d, 1H, J=8.1 Hz).

Example 4

Synthesis of 3-Chloro-2',6'-difluorobiphenyl-4-carbonitrile (EM-4977)

3-Chloro-2',6'-difluorobiphenyl-4-carbonitrile (EM-4977)

In an oven-dried flask purged with argon, a solution of 4-bromo-2-chlorobenzonitrile (268 mg, 1.238 mmol), 2,6-difluorophenylboronic acid (293 mg, 1.857 mmol), $Pd(PPh_3)_4$ (143 mg, 0.124 mmol) in toluene (10 mL) and EtOH (10 mL), and saturated solution of $NaHCO_3$ in water (1 mL) were refluxed while sterring for 5 h. The reaction mixture was poured into water and extracted 3 times with $CH_2Cl_2$. The organic layer was dried over magnesium sulfate, filtered and concentrated under reduced pressure. The crude compound was then purified by flash cromatography (diethyl ether-hexanes) to provide EM-4977 (45 mg, 15%) as a white solid. IR (KBr): 3072, 2237, 1626, 1602, 1578, 1468, 1386, 1231, 1058, 996, 888, 844, 783, 730, 693, 622, 516 $cm^{-1}$. $^1H$ RMN (400 MHz, acetone $d_6$) δ 7.23 (t, J=8 Hz, 2H), 7.60 (m, 1H), 7.73 (ddd, J=1.3, 1.4 & 8 Hz, 1H), 7.88 (d, J=1.3 Hz, 1H), 8.07 (d, J=8 Hz, 1H) ppm. $^{13}C$ RMN (75 MHz, $CDCl_3$) δ 112.06 (d, J=25 Hz), 112.14, 112.85, 115.83, 129.15, 130.80 (t, J=11 Hz), 131.73, 133.63, 135.40, 136.70, 159.63 (dd, J=7 & 250 Hz) ppm. GC/NCI/MS (m/e); 249 ($M^-$, 100).

PHARMACEUTICAL COMPOSITION EXAMPLES

Set forth below, by way of example and not of limitation, are several pharmaceutical compositions utilizing a preferred active compound EM-4283 for systemic use and EM-4977 for topical application. Other compounds of the invention or combination thereof, may be used in place of (or in addition to) EM-4283 or EM-4977. The concentration of active ingredient may be varied over a wide range as discussed herein. The amounts and types of other ingredients that may be included are well known in the art.

Example A

Composition Suitable for Injection

| Ingredient | Weight % (by weight of total composition) |
| --- | --- |
| EM-4283 | 0.4 |
| Ethanol | 6.4 |
| NaCl | 0.8 |
| Water | 91.5 |
| Benzyl alcohol | 0.9 |

Example B

Composition Suitable for Use as Topical Lotion

| Ingredient | Weight % (by weight of total composition) |
| --- | --- |
| EM-4977 | 1.0 |
| Ethanol | 70.0 |
| Propylene glycol | 29.0 |

Example C

Composition Suitable for Use as Topical Gel

| Ingredient | Weight % (by weight of total composition) |
| --- | --- |
| EM-4977 | 1.0 |
| Kucel | 1.5 |
| Ethanol | 70.0 |
| Propylene glycol | 27.5 |

Example D

Tablet

| Ingredient | Weight % (by weight of total composition) |
| --- | --- |
| EM-4283 | 20.0 |
| Gelatin | 5.0 |
| Lactose | 47.5 |
| Starch | 27.5 |

Example E

Gelatin Capsule

| Ingredient | Weight % (by weight of total composition) |
|---|---|
| EM-4283 | 20.0 |
| Lactose hydrous | 62.0 |
| Starch | 4.8 |
| Cellulose microcrystalline | 12.8 |
| Magnesium stearate | 0.4 |

Other antiandrogens may be substituted for EM-4283 or EM-4977 in the above formulations. For combination therapies, 5alpha, 17beta and/or PSRD1 could be added at weight % (with prorata reduction of other components).

Example F

Composition Suitable for Injection

| Ingredient | Weight % (by weight of total composition) |
|---|---|
| EM-4283 | 0.4 |
| Finasteride | 0.4 |
| Ethanol | 6.0 |
| NaCl | 0.8 |
| Water | 91.5 |
| Benzyl alcohol | 0.9 |

Example G

Composition Suitable for Use as Topical Lotion

| Ingredient | Weight % (by weight of total composition) |
|---|---|
| EM-4977 | 1.0 |
| Finasteride | 1.0 |
| Ethanol | 69.0 |
| Propylene glycol | 29.0 |

Example H

Composition Suitable for Use as Topical Gel

| Ingredient | Weight % (by weight of total composition) |
|---|---|
| EM-4977 | 20.0 |
| Finasteride | 1.0 |
| Kucel | 1.5 |
| Ethanol | 69.0 |
| Propylene glycol | 27.5 |

Example I

Tablet

| Ingredient | Weight % (by weight of total composition) |
|---|---|
| EM-4283 | 20.0 |
| Finasteride | 1.0 |
| Gelatin | 5.0 |
| Lactose | 46.5 |
| Starch | 27.5 |

Example J

Gelatin Capsule

| Ingredient | Weight % (by weight of total composition) |
|---|---|
| EM-4283 | 20.0 |
| Finasteride | 1.0 |
| Lactose hydrous | 61.0 |
| Starch | 4.8 |
| Cellulose microcystalline | 12.8 |
| Magnesium stearate | 0.4 |

Example K

Composition Suitable for Injection

| Ingredient | Weight % (by weight of total composition) |
|---|---|
| EM-4283 | 0.4 |
| EM-1404 | 0.4 |
| Ethanol | 6.0 |
| NaCl | 0.8 |
| Water | 91.5 |
| Benzyl alcohol | 0.9 |

Example L

Composition Suitable for Use as Topical Lotion

| Ingredient | Weight % (by weight of total composition) |
|---|---|
| EM-4977 | 1.0 |
| EM-1404 | 2.0 |
| Ethanol | 68.0 |
| Propylene glycol | 29.0 |

Example M

Composition Suitable for Use as Topical Gel

| Ingredient | Weight % (by weight of total composition) |
|---|---|
| EM-4977 | 1.0 |
| EM-1404 | 2.0 |
| Kucel | 1.5 |
| Ethanol | 68.0 |
| Propylene glycol | 27.5 |

Example N

Tablet

| Ingredient | Weight % (by weight of total composition) |
|---|---|
| EM-4283 | 20.0 |
| EM-1404 | 20.0 |
| Gelatin | 5.0 |
| Lactose | 27.5 |
| Starch | 27.5 |

Example O

Gelatin Capsule

| Ingredient | Weight % (by weight of total composition) |
|---|---|
| EM-4283 | 20.0 |
| EM-1404 | 20.0 |
| Lactose hydrous | 42.0 |
| Starch | 4.8 |
| Cellulose microcrystalline | 12.8 |
| Magnesium stearate | 0.4 |

Example P

Composition Suitable for Injection

| Ingredient | Weight % (by weight of total composition) |
|---|---|
| EM-4283 | 0.4 |
| EM-1791 | 0.4 |
| Ethanol | 6.0 |
| NaCl | 0.8 |
| Water | 91.5 |
| Benzyl alcohol | 0.9 |

Example Q

Composition Suitable for Use as Topical Lotion

| Ingredient | Weight % (by weight of total composition) |
|---|---|
| EM-4977 | 1.0 |
| EM-1791 | 2.0 |
| Ethanol | 68.0 |
| Propylene glycol | 29.0 |

Example R

Composition Suitable for Use as Topical Gel

| Ingredient | Weight % (by weight of total composition) |
|---|---|
| EM-4977 | 1.0 |
| EM-1791 | 2.0 |
| Ethanol | 68.0 |
| Propylene glycol | 27.5 |

Example S

Tablet

| Ingredient | Weight % (by weight of total composition) |
|---|---|
| EM-4283 | 20.0 |
| EM-1791 | 20.0 |
| Starch | 27.5 |
| Gelatin | 5.0 |
| Lactose | 27.5 |

Example T

Gelatin Capsule

| Ingredient | Weight % (by weight of total composition) |
|---|---|
| EM-4283 | 20.0 |
| EM-1791 | 20.0 |
| Lactose hydrous | 42.0 |
| Cellulose microcrystalline | 12.8 |
| Magnesium stearate | 0.4 |
| Starch | 4.8 |

The invention has been described in terms of preferred embodiments and examples, but is not limited thereby. Those of skill in the art will readily recognize the broader applicability and scope of the invention which is limited only by the patent claims that issue from this application or any patent application claiming priority (directly or indirectly) hereto.

What is claimed is:

1. A pharmaceutical composition comprising a pharmaceutically acceptable diluent or carrier and a therapeutically effective amount of at least one antiandrogenic compound of the molecular formula:

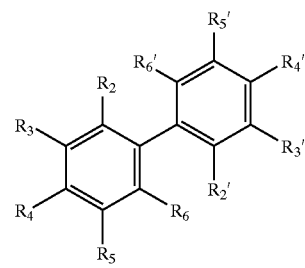

I

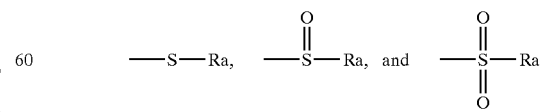

Wherein $R_2$, $R_3$, $R_5$ and $R_6$ are independently selected from the group consisting of hydrogen, fluoride, chloride, bromide, iodide, cyanide, $C_1$–$C_3$ alkyl, $C_1$–$C_3$ fluoroalkyl, nitro, carboxamide, (Ra being $C_1$–$C_3$ alkyl);

Wherein $R_4$ is cyanide;

Wherein $R_4'$ is selected from the group consisting of hydrogen, fluoride, chloride, bromide, iodide, cyanide,

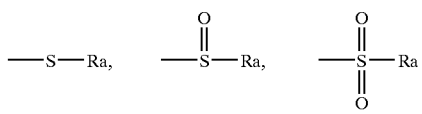

(Ra being $C_1$–$C_3$ alkyl), —ORb, —PO(ORb)$_2$, —C≡C—Rb, (Rb being $C_1$–$C_6$ alkyl), $C_2$–$C_3$ trifluorohydroxyalkyl, trifluoromethyl, nitro, amine, acetylamine, sulphamine, and ureide;

Wherein $R_2'$ and $R_6'$ are independently selected from the group consisting of hydrogen, fluoride, chloride, bromide, iodide, cyanide, trifluoromethyl, nitro, carboxamide,

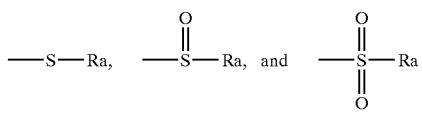

Wherein $R_3'$ and $R_5'$ are independently selected from the group consisting of hydrogen, fluoride, bromide, iodide, $C_2$–$C_3$ trifluorohydroxyalkyl, $C_1$–$C_3$ alkyl, $C_1$–$C_3$ fluoroalkyl, nitro, and carboxamide.

2. The pharmaceutical composition of claim 1 wherein $R_4'$ is cyanide.

3. The pharmaceutical composition of claim 2 having the following molecular formula:

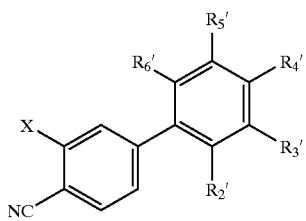

Wherein X is selected from the group consisting of fluoride, chloride, bromide, iodide, trifluoromethyl,

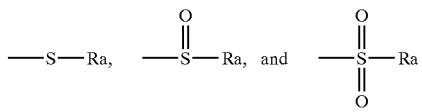

(Ra being $C_1$–$C_3$ alkyl);

Wherein $R_4'$ is selected from the group consisting of hydrogen, fluoride, chloride, bromide, iodide, cyanide, $C_2$—$C_3$ trifluorohydroxyalkyl, trifluoromethyl, nitro, amide, sulfamine,

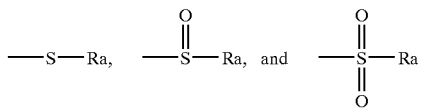

(Ra being $C_1$–$C_3$ alkyl).

4. A pharmaceutical composition of claim 1 having the following molecular structure:

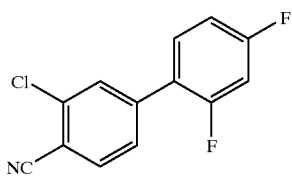

3-chloro-2',4'-difluoro-biphenyl-4-carbonitrile.

5. The pharmaceutical composition of claim 1 having the following molecular structure:

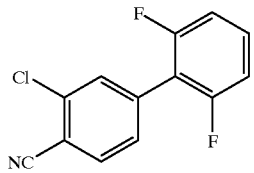

3-chloro-2',6'-difluoro-biphenyl-4-carbonitrile.

6. The pharmaceutical composition of claim 5 wherein said diluent or carrier is suitable for topical application.

7. The pharmaceutical composition of claim 1 wherein said diluent or carrier is suitable for oral administration.

8. A method of treating, or reducing the risk of developing prostate cancer, comprising administering to a patient in need of such treatment or reduction a therapeutically effective amount of the pharmaceutical composition of any of claims 1–4 or 7.

9. The method of claim 8, further comprising administering to said patient a therapeutically effective amount of at least one inhibitor selected from the group consisting of an inhibitor of type 5 17β-hydroxysteroid dehydrogenase, an inhibitor of 5α-reductase and an inhibitor of Prostate Short-Chain Dehydrogenase Reductase 1.

10. The method of claim 9, wherein an inhibitor of 5α-reductase and an inhibitor of type 5 17β-hydroxysteroid dehydrogenase are administered.

11. The method of claim 9, wherein an inhibitor of 5α-reductase and an inhibitor of Prostate Short-Chain Dehydrogenase Reductase 1 are administered.

12. The method of claim 9, wherein an inhibitor of type 5 17β-hydroxysteroid dehydrogenase and an inhibitor of Prostate Short-Chain Dehydrogenase Reductase 1 are administered.

13. The method of claim 8, further comprising administering to said patient therapeutically effective amounts of an inhibitor of type 5 17β-hydroxysteroid dehydrogenase, an inhibitor of 5α-reductase and an inhibitor of Prostate Short-Chain Dehydrogenase Reductase 1.

14. A method of treating, or reducing the risk of developing, benign prostatic hyperplasia comprising administering to a patient in need of such treatment or reduction, a therapeutically effective amount of the pharmaceutical composition of any of claims 1–4 or 7.

15. The method of claim 14, further comprising administering to said patient a therapeutically effective amount of at least one inhibitor selected from the group comprising an inhibitor of type 5 17β-hydroxysteroid dehydrogenase, an inhibitor of 5α-reductase and an inhibitor of Prostate Short-Chain Dehydrogenase Reductase 1.

16. The method of claim 15, wherein an inhibitor of 5α-reductase and an inhibitor of type 5 17β-hydroxysteroid dehydrogenase are administered.

17. The method of claim 15, wherein an inhibitor of 5α-reductase and an inhibitor of Prostate Short-Chain Dehydrogenase Reductase 1 are administered.

18. The method of claim 15, wherein an inhibitor of type 5 17β-hydroxysteroid dehydrogenase and an inhibitor of Prostate Short-Chain Dehydrogenase Reductase 1 are administered.

19. The method of claim 14, further comprising administering to said patient therapeutically effective amounts of an inhibitor of type 5 17β-hydroxysteroid dehydrogenase, an inhibitor of 5α-reductase and an inhibitor of Prostate Short-Chain Dehydrogenase Reductase 1.

20. A method of treating, or reducing the risk of developing, polycystic ovarian syndrome comprising administering to a patient in need of such treatment or reduction a therapeutically effective amount of the pharmaceutical composition of any of claims 1–4 or 7.

21. The method of claim 20, further comprising administering to said patient a therapeutically effective amount of at least one inhibitor selected from the group comprising an inhibitor of type 5 17β-hydroxysteroid dehydrogenase, an inhibitor of 5α-reductase and an inhibitor of Prostate Short-Chain Dehydrogenase Reductase 1.

22. The method of claim 21, wherein an inhibitor of 5α-reductase and an inhibitor of type 5 17β-hydroxysteroid dehydrogenase are administered.

23. The method of claim 21, wherein an inhibitor of 5α-reductase and an inhibitor of Prostate Short-Chain Dehydrogenase Reductase 1 are administered.

24. The method of claim 21, wherein an inhibitor of type 5 17β-hydroxysteroid dehydrogenase and an inhibitor of Prostate Short-Chain Dehydrogenase Reductase 1 are administered.

25. The method of claim 21, further comprising administering to said patient therapeutically effective amounts of an inhibitor of type 5 17β-hydroxysteroid dehydrogenase, an inhibitor of 5α-reductase and an inhibitor of Prostate Short-Chain Dehydrogenase Reductase 1.

26. A method of treating precocious puberty comprising administering to a patient in need of such treatment a therapeutically effective amount of the pharmaceutical composition of any of claims 1–4 or 7.

27. The method of claim 26, further comprising administering to said patient a therapeutically effective amount of at least one inhibitor selected from the group comprising an inhibitor of type 5 17β-hydroxysteroid dehydrogenase, an inhibitor of 5α-reductase and an inhibitor of Prostate Short-Chain Dehydrogenase Reductase 1.

28. The method of claim 27, wherein an inhibitor of 5α-reductase and an inhibitor of type 5 17β-hydroxysteroid dehydrogenase are administered.

29. The method of claim 27, wherein an inhibitor of 5α-reductase and an inhibitor of Prostate Short-Chain Dehydrogenase Reductase 1 are administered.

30. The method of claim 27, wherein an inhibitor of type 5 17β-hydroxysteroid dehydrogenase and an inhibitor of Prostate Short-Chain Dehydrogenase Reductase 1 are administered.

31. The method of claim 26, further comprising administering to said patient therapeutically effective amounts of an inhibitor of type 5 17β-hydroxysteroid dehydrogenase, an inhibitor of 5α-reductase and an inhibitor of Prostate Short-Chain Dehydrogenase Reductase 1.

32. A method of treating or reducing the risk of developing, acne, seborrhea, hirsutism or androgenic alopecia comprising administering to a patient in need of such treatment or reduction a therapeutically effective amount of the pharmaceutical composition of any of claims 1–3, 5 or 6.

33. The method of claim 32, further comprising administering to said patient therapeutically effective amount of at least one inhibitor selected from the group comprising an inhibitor of type 5 17β-hydroxysteroid dehydrogenase, an inhibitor of 5α-reductase and an inhibitor of Prostate Short-Chain Dehydrogenase Reductase 1.

34. The method of claim 33, wherein an inhibitor of 5α-reductase and an inhibitor of type 5 17β-hydroxysteroid dehydrogenase are administered.

35. The method of claim 33, wherein an inhibitor of 5α-reductase and an inhibitor of Prostate Short-Chain Dehydrogenase Reductase 1 are administered.

36. The method of claim 33, wherein an inhibitor of type 5 17β-hydroxysteroid dehydrogenase and an inhibitor of Prostate Short-Chain Dehydrogenase Reductase 1 are administered.

37. The method of claim 32, further comprising administering to said patient therapeutically effective amounts of an inhibitor of type 5 17β-hydroxysteroid dehydrogenase, an inhibitor of 5α-reductase and an inhibitor of Prostate Short-Chain Dehydrogenase Reductase 1.

38. A pharmaceutical composition comprising a pharmaceutically acceptable diluent or carrier and a therapeutically effective amount of at least one antiandrogenic compound of the molecular formula:

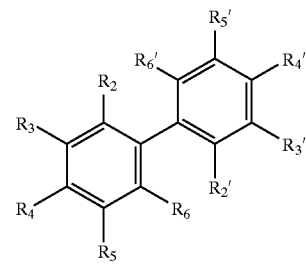

Wherein $R_2$, $R_3$, $R_5$ and $R_6$ are independently selected from the group consisting of hydrogen, fluoride, chloride, bromide, iodide, cyanide, trifluoromethyl, nitro, and carboxamide,

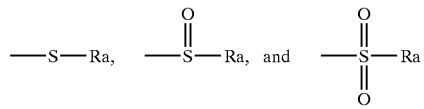

(Ra being $C_1$–$C_3$ alkyl);
Wherein $R_4$ and $R_4'$ are independent selected from the group consisting of hydrogen, fluoride, chloride, bromide, iodide, cyanide,

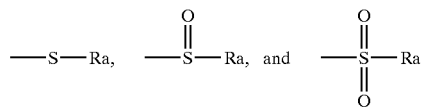

(Ra being $C_1$–$C_3$ alkyl), —ORb, —PO(ORb)$_2$, —C≡C—Rb, (Rb being $C_1$–$C_6$ alkyl), $C_2$–$C_3$ trifluorohydroxyalkyl, trifluoromethyl, nitro, amine, acetylamine, sulphamine, and ureide;
Wherein at least one of $R_4$ and $R_4'$ is not hydrogen;
Wherein $R_2'$ and $R_6'$ are independently selected from the group consisting of hydrogen, fluoride, chloride, bromide, iodide, cyanide, trifluoromethyl, nitro, carboxamide, —S—Ra,

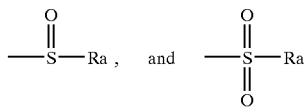

(Ra being $C_1$–$C_3$ alkyl);

Wherein $R_3'$ and $R_5'$ are independently selected from the group consisting of hydrogen, fluoride, chloride, bromide, iodide, cyanide, $C_2$–$C_3$ trifluorohydroxyalkyl, trifluoromethyl, nitro, and carboxamide.

39. A pharmaceutical composition comprising a pharmaceutically acceptable diluent or carrier and a therapeutically effective amount of at least one antiandrogenic compound having the following molecular structure:

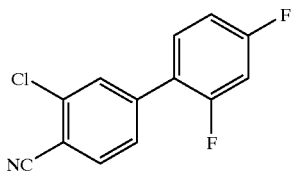

3-chloro-2',4'-difluoro-biphenyl-4-carbonitrile.

40. A method of treating or reducing the risk of developing, acne, seborrhea, hirsutism or androgenic alopecia comprising administering to a patient in need of such treatment or reduction of a therapeutically effective amount of the pharmaceutical composition of any of claims 1–3, 5 or 6.

* * * * *